(12) United States Patent
Terry et al.

(10) Patent No.: US 6,426,099 B1
(45) Date of Patent: Jul. 30, 2002

(54) HERBAL FORMULATION FOR REBUILDING INTESTINAL BACTERIA

(75) Inventors: Travis L. Terry, Clearwater; Tommy Stanley Watson; Brenda F. Watson, both of Tarpon Springs, all of FL (US)

(73) Assignee: Renew Life, Inc., Clearwater, FL (US)

( * ) Notice: Subject to any disclaimer, the term of this patent is extended or adjusted under 35 U.S.C. 154(b) by 0 days.

(21) Appl. No.: 09/204,036

(22) Filed: Dec. 1, 1998

Related U.S. Application Data

(60) Provisional application No. 60/067,271, filed on Dec. 3, 1997.

(51) Int. Cl.$^7$ .......................... A61K 35/78; A61K 38/54
(52) U.S. Cl. ...................... 424/768; 424/725; 424/94.2; 424/94.21; 424/94.63; 424/94.65; 424/94.66; 514/556

(58) Field of Search .............................. 424/195.1, 94.2, 424/94.21, 94.61, 94.63, 94.65, 94.66, 725, 768; 514/556

(56) References Cited

U.S. PATENT DOCUMENTS

| | | | | |
|---|---|---|---|---|
| 4,447,412 A | * | 5/1984 | Bilton | 424/16 |
| 4,755,504 A | * | 7/1988 | Liu | 514/26 |
| 4,871,574 A | * | 10/1989 | Yamazaki et al. | 426/622 |
| 5,397,778 A | * | 3/1995 | Forse et al. | 514/198 |

\* cited by examiner

*Primary Examiner*—Francisco Prats
(74) *Attorney, Agent, or Firm*—Donald R. Fraser

(57) ABSTRACT

An herbal formulation comprises betaine HCl, plant enzymes, papain, probiotic micro flora, fruitooligosaccharides, l-glutamine, quercitin, butyric acid, borage seed, flax seed, lecithin, gamma oryzanol, bromelain, pepsin, and N-acetylglucosamine.

14 Claims, No Drawings

HERBAL FORMULATION FOR REBUILDING INTESTINAL BACTERIA

This is a continuation of provisional application Ser. No. 60/067,271 filed Dec. 3, 1997.

FIELD OF THE INVENTION

This invention relates generally to an herbal food supplement and formulation for rebuilding intestinal bacteria. More particularly, the invention is directed to a probiotic formulation containing plant enzymes and micro flora effective for reestablishing healthy intestinal bacteria and rebuilding intestinal mucosa.

BACKGROUND OF THE INVENTION

Herbal formulations can provide a supplement to the daily human diet, and additionally can provide a natural method for reestablishing and rebuilding intestinal bacteria and mucosa. This is especially important following the use of an intestinal tract cleanser which often is used to treat a condition known as "leaky gut."

Leaky gut is a condition in which the mucosa of the intestinal tract is compromised, thereby allowing toxins and food particles to penetrate the lining of the intestinal tract and enter the body's blood stream. The body itself may naturally attempt to counteract this phenomenon, usually with several negative side effects. Firstly, the body may attempt to produce antibodies to combat the toxins. This will result in the body developing allergies to the foods which have caused the breakdown of the intestinal tract lining. Furthermore, the liver may increase its production of detoxifying enzymes. The activation of some of these enzymes may release harmful free radicals as a byproduct. These oxidizing free radicals may, in turn, damage the liver and other tissues, resulting in a weakened immune system.

Symptoms of leaky gut may include irritable bowel disease, chronic fatigue, food allergies, and arthritis.

Following treatment for leaky gut, in which the intestinal tract is cleansed of parasites and candida, the intestinal bacteria and mucosa must be reestablished for good health.

It would be desirable to prepare an herbal formulation which would act as a food supplement as well as reestablish healthy levels of intestinal bacteria and rebuild intestinal mucosa, thereby rejuvenating the intestinal tract lining to diminish the passage therethrough of toxins and food particles.

SUMMARY OF THE INVENTION

Accordant with the present invention, there surprisingly has been discovered an herbal formulation which acts as a food supplement, and is useful for reestablishing intestinal bacteria. The herbal formulation comprises:

betaine HCl;
plant enzymes;
papain;
probiotic micro flora;,
fruitooligosaccharides
l-glutamine;
quercitin;
butyric acid;
borage seed;
flax seed;
lecithin; and a mixture of gamma oryzanol, bromelain, pepsin, and N-acetylglucosamine.

The herbal formulation of the present invention is useful as a food supplement, and additionally is particularly useful for reestablishing healthy levels of intestinal bacteria and rebuilding intestinal mucosa following treatment to cleanse the body's intestinal tract.

DETAILED DESCRIPTION OF THE PREFERRED EMBODIMENT

The present invention is directed to an herbal formulation useful as a food supplement and for reestablishing intestinal bacteria. The herbal formulation comprises betaine HCl, plant enzymes, papain, probiotic micro flora, fruitooligosaccharides, l-glutamine quercitin, butyric acid, borage seed, flax seed, lecithin, gamma oryzanol, bromelain, pepsin, and N-acetylglucosamine. All of the recited ingredients are well-known in the food supplements and nutrition industry.

The inventive formulation may be mixed together, compressed, and formed into a capsule which may be taken orally.

Betaine HCl is present in the inventive formulation, acting as an agent for reestablishing proper pH balance within the intestinal tract. The hydrochloric acid comprises from about 25 to about 35 weight percent of the herbal formulation.

Plant enzymes are present in the inventive formulation, acting as a digestive aid. Suitable plant enzymes include, but are not necessarily limited to, amylase, protease, lipase, lactase, cellulase, invertase, maltase, pectinase, and phytase, as well as mixtures thereof. The plant enzymes comprise from about 2 to about 7 weight percent of the herbal formulation.

Papain is present in the inventive formulation, acting as a digestive aid. The papain comprises from about 1 to about 4 weight percent of the herbal formulation.

Probiotic micro flora (acidophilus and bifido bacteria) are present in the inventive formulation, acting as an agent for reestablishing good flora balance. The probiotic flora comprises from about 0.5 to about 5 weight percent of the herbal formulation.

fructooligosaccharides is present in the inventive formulation, acting as an agent to promote micro flora growth. The frutooligosaccharides comprises from about 2 to about 7 weight percent of the herbal formulation.

L-glutamine is present in the inventive formulation, acting as an agent to assist the healthy functioning of the intestinal tract. The l-glutamine comprises from about 5 to about 15 weight percent of the herbal formulation.

Quercitin is present in the inventive formulation, acting as an agent to stabilize the intestinal membrane. The quercitin comprises from about 2 to about 7 weight percent of the herbal formulation.

Butyric acid is present in the inventive formulation, acting as an agent to restore the gastrointestinal mucosa. The butyric acid comprises from about 2 to about 7 weight percent of the herbal formulation.

Borage seed is present in the inventive formulation, acting as an agent to reduce intestinal inflammation. The borage seed comprises from about 5 to about 15 weight percent of the herbal formulation.

Flax seed is present in the inventive formulation, acting as an agent for rebuilding the intestinal mucosa. The flax seed comprises from about 5 to about 15 weight percent of the herbal formulation.

Lecithin is present in the inventive formulation, acting as an agent for restoring gastrointestinal mucosa. The lecithin comprises from about 5 to about 10 weight percent of the herbal formulation.

A mixture of gamma oryzanol, bromelain, pepsin, and N-acetylglucosamine is present in the inventive formulation, acting as an aid to the growth of intestinal bacterial and the formation of intestinal mucosa. Each component many be present in the mixture at a concentration ranging from about 5 to about 75 weight percent. The mixture comprises from about 5 to about 15 weight percent of the herbal formulation.

The effective dosage for the food supplement and formulation for rebuilding intestinal bacteria according to the present invention is about 750 mg. following each meal. Preferably, the effective dosage is about 2,250 mg./day. The food supplement and formulation for rebuilding intestinal bacteria according to the present invention is taken orally.

The invention is more easily comprehended by reference to the specific embodiments recited hereinabove which are representative of the invention. It must be understood, however, that the specific embodiments are provided only for the purpose of illustration, and that the invention may be practiced otherwise than as specifically illustrated without departing from its spirit and scope.

What is claimed is:

1. An herbal formulation, comprising:
   betaine HCl;
   plant enzymes;
   papain;
   probiotic micro flora;
   fructooligasaccharides
   l-glutamine;
   quercitin;
   butyric acid;
   borage seed;
   flax seed;
   lecithin; and
   a mixture of gamma oryzanol, bromelain, pepsin, and N-acetylglucosamine.

2. The herbal formulation according to claim 1, wherein the concentration of betaine HCl ranges from about 25 to about 35 weight percent.

3. The herbal formulation according to claim 1, wherein the concentration of plant enzymes ranges from about 2 to about 7 weight percent.

4. The herbal formulation according to claim 1, wherein the concentration of papain ranges from about 1 to about 4 weight percent.

5. The herbal formulation according to claim 1, wherein the concentration of probiotic micro flora ranges from about 0.5 to about 5 weight percent.

6. The herbal formulation according to claim 1, wherein the concentration of fructooligosaccharides from about 2 to about 7 weight percent.

7. The herbal formulation according to claim 1, wherein the concentration of l-glutamine ranges from about 5 to about 15 weight percent.

8. The herbal formulation according to claim 1, wherein the concentration of quercitin ranges from about 2 to about 7 weight percent.

9. The herbal formulation according to claim 1, wherein the concentration of butyric acid ranges from about 2 to about 7 weight percent.

10. The herbal formulation according to claim 1, wherein the concentration of borage seed ranges from about 5 to about 15 weight percent.

11. The herbal formulation according to claim 1, wherein the concentration of flax seed ranges from about 5 to about 15 weight percent.

12. The herbal formulation according to claim 1, wherein the concentration of lecithin ranges from about 5 to about 10 weight percent.

13. The herbal formulation according to claim 1, wherein the concentration of the mixture of gamma oryzanol, bromelain, pepsin, and N-acetylglucosamine ranges from about 5 to about 15 weight percent.

14. An herbal formulation for reestablishing intestinal bacteria, comprising:
   from about 25 to about 35 weight percent betaine HCl;
   from about 2 to about 7 weight percent plant enzymes;
   from about 1 to about 4 weight percent papain;
   from about 0.5 to about 5 weight percent probiotic micro flora;
   from about 2 to about 7 weight percent fructooligasaccharides;
   from about 5 to about 15 weight percent l-glutamine;
   from about 2 to about 7 weight percent quercitin;
   from about 2 to about 7 weight percent butyric acid;
   from about 5 to about 15 weight percent borage seed;
   from about 5 to about 15 weight percent flax seed;
   from about 5 to about 10 weight percent lecithin; and
   from about 5 to about 15 weight percent of a mixture of gamma oryzanol, bromelain, pepsin, and N-acetylglucosamine.

* * * * *